United States Patent
Mashinchi et al.

(10) Patent No.: US 9,646,073 B2
(45) Date of Patent: May 9, 2017

(54) EVENT DETECTION ALGORITHMS

(75) Inventors: Mohammad Hadi Mashinchi, North Bondi (AU); David Albert Barda, Rose Bay (AU); Jian Huang, North Sydney (AU)

(73) Assignee: Fred Bergman Healthcare Pty. Ltd., North Sydney (AU)

(*) Notice: Subject to any disclaimer, the term of this patent is extended or adjusted under 35 U.S.C. 154(b) by 536 days.

(21) Appl. No.: 14/130,833

(22) PCT Filed: Jul. 5, 2012

(86) PCT No.: PCT/AU2012/000806
§ 371 (c)(1),
(2), (4) Date: Apr. 29, 2014

(87) PCT Pub. No.: WO2013/003905
PCT Pub. Date: Jan. 10, 2013

(65) Prior Publication Data
US 2014/0244644 A1    Aug. 28, 2014

Related U.S. Application Data

(60) Provisional application No. 61/544,340, filed on Oct. 7, 2011, provisional application No. 61/505,082, filed on Jul. 6, 2011.

(51) Int. Cl.
*G06F 17/30* (2006.01)
*G06Q 50/22* (2012.01)
*A61F 13/42* (2006.01)

(52) U.S. Cl.
CPC ....... *G06F 17/30595* (2013.01); *G06Q 50/22* (2013.01); *A61F 13/42* (2013.01)

(58) Field of Classification Search
None
See application file for complete search history.

(56) References Cited

U.S. PATENT DOCUMENTS 4,846,190 A * 7/1989 John ............ A61B 5/04021
600/544
5,500,855 A    3/1996 Hershey et al.
(Continued)

FOREIGN PATENT DOCUMENTS

WO     2007102842 A2     9/2007
WO     WO 2007102842 A2 *  9/2007 ......... A61B 5/14532

OTHER PUBLICATIONS

International Search Report for PCT/AU2012/000806 dated, Aug. 31, 2012.

*Primary Examiner* — Syed Hasan
(74) *Attorney, Agent, or Firm* — Hansen IP Law PLLC

(57) ABSTRACT

A method for analyzing incoming data, comprising the steps of processing the incoming data in segments to output a sequence of segment types by extracting one or more properties of an incoming data segment and forming an Unknown Property Vector for each segment of data in the incoming data, and processing the sequence of segment types to identify events in the incoming data. The sequence of segment types is determined, for each segment, by reference to a set of Reference Property Vectors that are relevant to the Unknown Property Vector. This may involve application of first and/or second and/or further functions to identify at least a first subset of Reference Property Vectors that are relevant to the Unknown Property Vector. Alternatively, a logistic regression algorithm, derived using clustering or classification methods for identifying candidate vectors, may be used.

30 Claims, 6 Drawing Sheets

(56) References Cited

U.S. PATENT DOCUMENTS

| | | |
|---|---|---|
| 2004/0073098 A1 | 4/2004 | Geva et al. |
| 2004/0243328 A1* | 12/2004 | Rapp ............... A61B 5/4094 702/71 |
| 2007/0270774 A1 | 11/2007 | Bergman et al. |
| 2008/0010641 A1* | 1/2008 | Zhao ............... G05B 23/0264 718/101 |

* cited by examiner

| Event Sequence Identifier | Peak value of the previous event | Length from the previous peak | Windows properties | Segment's type |
|---|---|---|---|---|
| 1 | x | x | x | 1 |
| 1 | x | x | x | 2 |
| 2 | x | x | x | 1 |
| 2 | x | x | x | 1 |
| 2 | x | x | x | 2 |
| 2 | x | x | x | 1 |
| 3 | x | x | x | 2 |
| 4 | x | x | x | 1 |
| 4 | x | x | x | 0 |

| Event Sequence Identifier | Peak value of the previous event | Length from the previous peak | Windows properties | Segment type |
|---|---|---|---|---|
| 2 | x | x | x | 1 |
| 2 | x | x | x | 1 |
| 2 | x | x | x | 2 |
| 2 | x | x | x | 1 |

Figure 9

| Event Sequence Identifier | Peak value of the previous event | Length from the previous peak | Windows properties | Segment type | Euclidian distance |
|---|---|---|---|---|---|
| 2 | x | x | x | 1 | 1.7 |
| 2 | x | x | x | 1 | 1.8 |
| 2 | x | x | x | 2 | 1.3 |
| 2 | x | x | x | 1 | 1.1 |

Figure 10

| Event Sequence Identifier | Peak value of the previous event | Length from the previous peak | Windows properties | Segment type | Euclidian distance |
|---|---|---|---|---|---|
| 2 | x | x | x | 1 | 1.1 |
| 2 | x | x | x | 2 | 1.3 |
| 2 | x | x | x | 1 | 1.7 |
| 2 | x | x | x | 1 | 1.8 |

Figure 11

| Event Sequence Identifier | Peak value of the previous event | Length from the previous peak | Windows properties | Segment type | Euclidian distance |
|---|---|---|---|---|---|
| 2 | x | x | x | 1 | 1.1 |
| 2 | x | x | x | 1 | 1.2 |
| 2 | x | x | x | 2 | 1.3 |

Figure 12

EVENT DETECTION ALGORITHMS

FIELD OF THE INVENTION

This invention relates to methods, systems and computer program products and related aspects for improving event detection using signals obtained from sensors. The invention relates particularly but not exclusively to processing of sensor signals obtained from wetness sensors such as those that may be employed to detect wetness in incontinence pads, diapers, nappies, wound dressings and the like.

BACKGROUND TO THE INVENTION

Incontinence is a condition in which there is an uncontrolled release of discharges or evacuations. Urinary incontinence refers to loss of bladder control resulting in involuntary or uncontrolled urination. Other forms of incontinence include faecal or bowel incontinence.

Treatment options for incontinence can include behaviour management, medication and surgery. In circumstances where treatment is not available or unsuccessful, the only option is to address the incontinence events themselves. Such methods include the incontinent individual wearing an absorbent pad, diaper or nappy.

Most incontinent individuals are elderly or suffer from some form of disability or cognitive impairment. Accordingly, a significant proportion of incontinent individuals reside in care institutions such as nursing homes, aged care facilities and geriatric institutions as well as hospitals. Many of these individuals suffer from incontinence events on a regular basis. Additionally, infants and toddlers are incontinent individuals who, although they typically do not reside in care institutions, may benefit from the present invention.

To comply with care regulations and protocols it is necessary for staff to conduct manual checks of incontinent individuals on a regular basis. These manual checks are typically carried out irrespective of whether the individual has actually suffered an incontinence event. Often, the individual is unwilling or unable to cooperate and/or alert staff of the fact that an incontinence event has occurred. As can be appreciated, the need to conduct regular checks of individuals for the occurrence of an incontinence event places a significant burden on the resources of care institutions and also causes interruption to the individual's day to day activities, including their rest and sleep.

Incontinence indicators and detection systems exist. However, generally these are unable to distinguish e.g. a urinary incontinence event from a faecal incontinence event. Furthermore, existing incontinence detection systems are typically unable to detect or provide useful information about individual events such as the volume of a particular event. Most often, existing incontinence detection systems merely alert carers to the occurrence of an event so that the carer may then attend to changing of the pad or diaper. However, often times the incontinence event may not be significant enough to warrant changing of the diaper. Accordingly, the alerting system may lead to loss of time and/or resources.

Attempts to refine existing systems or to develop new systems which provide improved and/or enhanced wetness event detection have been frustrated by difficulties in sensor signal processing, producing erroneous and often useless results. As a result, such systems have failed once deployed in actual care scenarios and carers revert to the traditional methods of manual checking. The present invention seeks to ameliorate or improve upon signal processing that may be used to provide improved wetness detection systems, particularly as may be applied in monitoring individuals who experience the condition of incontinence.

The discussion of the background to the invention included herein including reference to documents, acts, materials, devices, articles and the like is intended to explain the context of the present invention. This is not to be taken as an admission or a suggestion that any of the material referred to was published, known or part of the common general knowledge as at the priority date of any of the claims.

SUMMARY OF THE INVENTION

Viewed from one aspect, the present invention provides a method for analysing incoming data, comprising the steps of: (a) processing the incoming data in segments to output a sequence of segment types by extracting one or more properties of an incoming data segment and forming an Unknown Property Vector, for each segment of data in the incoming data; and (b) processing the sequence of segment types to identify events in the incoming data; wherein the sequence of segment types is determined, for each segment, by reference to a set of Reference Property Vectors that are Relevant to the Unknown Property Vector.

The incoming data may be data from any source. In a preferred embodiment, the incoming data is sensor data from a wetness sensor, and the events identified are wetness events. It is to be understood, however that wetness-related events such as odour events or audible events may be identified in addition to or as an alternative to detection of wetness per se, employing the methods, systems and other aspects of the present invention.

In one embodiment, processing the incoming data in segments includes applying a first function on the Unknown Property Vector and a set of Reference Property Vectors to identify at least a first subset of Reference Property Vectors that are relevant to the Unknown Property Vector. The first function may be any function capable of determining relationships (such as similarities) between data and may be an algorithm comprising a plurality of more basic functions, or a single, more complex function which may, in some forms, be expressed mathematically. Thus the first function may include aspects from algorithms such as but not limited to those known as K-nearest neighbours (K-NN), decision trees, support vector machine (SVM), neural network algorithms, clustering and classification methods and the like. Optionally, a second (and optionally third/fourth/subsequent) function may be applied on at least a second subset of the Reference Property Vectors (and third/fourth/subsequent subsets) to determine a segment type for the Unknown Property Vector.

In another embodiment, processing the incoming data in segments involves applying a logistic regression algorithm which is derived by creating, using a clustering or classification or other similar method or combination of methods, one or more candidate vectors representing a reduced set or the complete set of Reference Property Vectors. The one or more candidate vectors contain vector elements, each of which represents a degree of belonging to each of a plurality of different segment types. The candidate vectors are then used to generate the logistic regression function which is applied to the incoming data to determine the segment type when incoming data is analysed. This is discussed in more detail below.

In a preferred embodiment, the Reference Property Vectors are obtained from segmented reference data and each segment in the reference data has a pre-determined segment type which is associated with the Reference Property Vector. It is to be understood, however that in some instances it is not possible to determine a particular segment type for a segment of reference data with absolute certainty and so, the pre-determined segment-type associated with a Reference Property Vector may itself be a vector (i.e. a segment-type vector) which represents a likelihood of that segment belonging to each of a plurality of different segment types. Association is preferably by way of an identifier (or a vector) in an entry of the Reference Property Vector. Ideally, the incoming data and preferably the reference data is smoothed before being segmented, however in another embodiment it is possible to do segmentation without smoothing.

The first and the second functions may be applied to a complete collection of Reference Property Vectors representing the reference data. However, in some embodiments the complete collection may comprise a very large dataset. Accordingly, in some embodiments it may be desirable for the first and the second functions to be applied to only a subset of Reference Property Vectors in the complete collection. That set need not comprise sequential Reference Property Vectors from the complete collection. In an embodiment, the set may, comprise e.g. 10% or 20% or 30% or some other proportion of the complete collection of Reference Property Vectors selected at random or quasi-random or using some other approach, from the complete set. In another embodiment the first and second functions may be applied to a set of representative candidate vectors that represent the complete collection of Reference Property Vectors. The representative candidate vectors may be determined by dividing the complete set into a number of groups (e.g. using a classification or clustering method) where each group is represented by a vector representing the degree of belonging of each cluster/group to each of the segment types represented in the vector constituents. The first and the second functions can then be applied to the representative candidate vectors for each group.

The first subset of Reference Property Vectors comprises vectors which have a similarity with or relationship to properties associated with the Unknown Property Vector. Thus, the first subset of Reference Property Vectors may also be referred to as "relevant" Reference Property Vectors. In an embodiment, the first subset of Reference Property Vectors is generated by applying the first function on the Unknown Property Vector and a set of Reference Property Vectors to determine e.g. a relevancy ratio. Ideally, a relevancy ratio is calculated for each of the vectors in the set of Reference Property Vectors, the relevancy ratio describing the relevance of each of those vectors (or the data they represent) to the Unknown Property Vector. The relevancy ratio may be e.g. a weighting or percentage which facilitates ranking of each vector in the set of Reference Property Vectors according to its relevance or relationship (e.g. similarity with) the Unknown Property Vector. The term "relevancy ratio" merely refers to an indicator of the extent of the relevance of a Reference Property Vector to the Unknown Property Vector. It may be calculated using any methods such as Euclidean-based methods, clustering methods, classification methods, granular computing or any method that computes similarity (or dissimilarity of two or more vectors).

A second function may be applied, which determines a segment type for the Unknown Property Vector and may employ any suitable approach. In one embodiment, the second function is applied on a second subset of relevant Reference Property Vectors which is derived from the complete collection of Reference Property Vectors (i.e. a subset of the complete collection of Reference Property Vectors) to determine a segment type for each of the segments in the incoming data. In one embodiment, the second subset is obtained by applying a function on the first subset of Reference Property Vectors as well as the Unknown Property Vector. It is to be understood, that the first subset and the second subset of Reference Property Vectors may be the same, or they may be mutually exclusive. In other embodiments, the first subset itself is a subset of the second subset or vice versa. For example the second subset could be a subset of the first subset in the scenario where some of the vectors of the first subset are discarded because they are not considered to be sufficiently "relevant" to the Unknown Property Vector. In a more general case third, fourth and further functions may be applied on the third, fourth and other subsets. Applying further functions may lead to obtaining more and better subsets, with each function applied.

The second function may include aspects from algorithms such as but not limited to those known as K-nearest neighbours (K-NN), decision trees, support vector machine (SVM), neural network algorithms, clustering and classification algorithms, logistic regression and the like.

In another embodiment, the second function may be applied on the second subset of Reference Property Vectors (or the complete collection, which includes the second subset) and their relevancy ratios (determined with respect to the Unknown Property Vector) to determine segment type for each of the segments in the incoming data. In the latter method, the complete collection or the full set of Reference Property Vectors may be used because the relevancy ratio diminishes the influence of Reference Property Vectors that have lower relevance to the Unknown Property Vector when determining segment type.

In a preferred embodiment, incoming data is segmented and one or more properties are extracted using a moving window. The moving window may be described as having one or more of a width w and a height h. Ideally, segments are selected for processing by shifting the moving window by an offset of X seconds. Windows of segmented data may be processed sequentially, or out of sequential order (e.g. in random or somewhat-random order) although sequential processing typically leads to computational efficiency which may improve overall system performance. One or more of the offset X, width w and height h may be determined dynamically, or may have a static value. Dynamic determination of these parameters may involve e.g. applying a function, such as a window constraint function, on a plurality of earlier segments, or applying a function which is determined by a user as a result of trial and error or experimentation.

It is to be understood that various aspects of the present invention employ parameters. It is to be understood that while those parameters may be referred to as representing a value, that value need not be limited to a static value. Rather, the value may be dynamically determined, e.g. using a function applied on previous data or data segments or a function applied on other data or data segments.

A segment type determined for data corresponding to the Unknown Property Vector may be e.g. a value which provides a deterministic indicator of the segment type. In an embodiment, a segment type is selected from the group including: "flat" having a segment type identifier 0; "Before Peak" having a segment type identifier +1; and "After Peak" having a segment type identifier −1. Optionally, there may be a segment type referred to as "unknown" which is used when the data cannot reliably lead to a conclusion for a particular segment's type. An unknown segment type may have a segment type identifier of 0 or null. Similar identifiers may be utilised in segment type vectors which represent a likelihood of a segment belonging to each of a plurality of different segment types. For example, a segment type vector [1, 0, 0] may represent a segment of the type "Before Peak" with 100% certainty. Alternatively a segment type vector [0.2, 0.3, 0.5] may represent a segment which has 20% degree of belonging in "Before Peak", 30% degree of belonging in "After Peak" and 50% belonging in "flat" segment types, degree of belonging is a probabilistic indicator of the likelihood that the segment is of a particular "type".

Ideally, properties represented by the property vectors include one or more of: intrinsic properties; extrinsic properties; and may also incorporate demographic information. In one embodiment, one of the properties represented in a property vector is a sequence identifier representing the sequence number of an event in an event cycle. The event sequence identifier may be determined based on the number of events that have already been detected in a pad cycle. For example, for an Unknown Property Vector having Sequence ID=3 represents a third event occurring in a sequence of events.

In one embodiment, the first function is used to give a weighting to each of the Reference Property Vectors based on similarity between the sequence identifier of Reference Property Vector and a sequence identifier of the Unknown Property Vector. Thus, by way of example if an Unknown Property Vector has Sequence ID=3, any Reference Property Vector also having Sequence ID=3 is allocated a weighting=1. Reference Property Vectors having a Sequence ID=2 or 4 may be allocated a weighting of 0.5 whereas Reference Property Vectors having Sequence ID=1 or 6 may be allocated a weighting of zero. The influence of Reference Property Vectors having a weighting of zero is diminished or eliminated, whereas the impact of the remaining vectors is modified in accordance with their weighting.

The first function may alternatively/additionally give a weighting to each of the Reference Property Vectors based on a similarity between a property (or a plurality of properties) other than sequence identifier. Weighting a vector based on sequence identifier similarity is only one example of hierarchical ranking which may be employed in various facets of the present invention. Another example is hierarchical ranking based on Euclidian distance (discussed below) although it is to be understood that applying hierarchical ranking to any property or group of properties is possible.

In one embodiment, the method includes correcting for an imbalance in the number of occurrences of each segment type in the set of Reference Property Vectors, relative to the total number of vectors in the set of Reference Property Vectors (representing the reference data). This correcting step may be incorporated into e.g. the second function.

In a preferred embodiment, the first function may also be used to perform the steps of calculating a distance between corresponding properties in the Unknown Property Vector and each of a plurality of Reference Property Vectors; and identifying Reference Property Vectors as being in the first subset where the distance calculated is within a limit. Reference Property Vectors falling outside the limit may be excluded from consideration. Alternatively, a weighting may be applied to the vector, based on the calculated distance and this can diminish the influence of more distant Reference Property Vectors to the unknown vector (e.g. more than a limit) on the analysis. A limit may be user-defined, or it may be dynamically determined e.g. based on earlier incoming data or other data. Preferably, the distance calculated is a Euclidian distance measuring similarity between properties in the Unknown Property Vector and corresponding properties in the plurality of Reference Property Vectors.

Processing the sequence of segment types enables identification of events in the incoming data. In some embodiments it may also facilitate determining properties of events, such as event volume and duration. Ideally, processing the sequence of segment types includes identifying in the sequence a sub-sequence of segment types that correspond to one of Flat event stage, Before Peak stage, Event Peak stage, and After Peak stage. This may be done using any suitable test, several of which are exemplified herein. In one embodiment, processing the sequence of segment types includes:

(a) for each segment in the sequence, determining T by applying a first test function on a subset of segment type identifiers in the sequence; and (b) comparing T to a first threshold, $\alpha$, to identify that the subsequence of segment types corresponds to the Before Peak stage; and/or (c) comparing T to a second threshold, $\beta$, to identify that the subsequence of segment types corresponds to the After Peak stage;

In an embodiment, the first test function determines T as the sum or the average of current segment type identifier and the previous l segment type identifiers. Alternatively, the first test function may determine T using another method, such as a probabilistic method where T is calculated as a value between zero and one which represents the likelihood of a group of segments being of a particular type.

In one embodiment, step (b) above involves, if T is greater than or equal to a then satisfying a Before Peak Test for the segment; and step (c) above involves, if T is less than or equal to $\beta$ then satisfying an After Peak Test for the segment. Processing the sequence of segment types may further involve (d) for $\alpha > T > \beta$, satisfying a Peak Test designating an event peak stage for the segment.

In an embodiment where the allocated segment types are segment-type vectors, processing the sequence of segment-type vectors may include:

a) for each segment-type vector in the sequence, determining P by applying a second test function on a subset of segment type vectors in the sequence;

b) if the segment type identified in (a) is Before Peak, compare P to a first threshold, A, to identify that the subsequence of segment types corresponds to the Before Peak stage; and c) if the segment type identified in (a) is After Peak, compare P to a second threshold, B, to identify that the subsequence of segment types corresponds to the After Peak stage.

In one embodiment for processing segment-type vectors, the second test function is applied to the current segment-type vector and previous l segment-type vectors in the sequence and determines a representative segment-type vector. This may be performed on the l vectors in the order in which they appear in the sequence, or in some other order, or on a subset of the l vectors. The representative segment-type vector is calculated to determine which of the segment types referred to in all of the segment type vectors has the highest likelihood of occurrence, and then providing a value for P which represents the highest likelihood. This may be done in a number of different ways. For example, the second test function may determine an average across all of the segment type vectors in the sequence and determine the segment type with the highest likelihood of occurrence to provide a value for P, or it could determine the likelihood of the segment types having highest probability in each of the segment-type vectors to calculate P. It is to be understood however, that in another embodiment, P, A and B are vectors, not absolute values. In such an embodiment, P is the representative segment-type vector.

In an embodiment (b) above involves, if the segment type identified in (a) is Before Peak and P is greater than A, then satisfying a Before Peak Test for the segment; and step (c) above involves, if the segment type identified in (a) is After Peak and P is greater than B, then satisfying an After Peak Test for the segment.

One or more of l, $\alpha$, $\beta$, A and B may be dynamically determined, e.g. using a function applied over a plurality of earlier segments or a function determined by trial and error or experimentation. In another embodiment, one or more of l, $\alpha$, $\beta$, A and B are static values and may be user-definable. In yet another embodiment control variables that may be optimised, such as the values of one or more of l, $\alpha$, $\beta$, A and B, are determined during assessment (live-optimization) or in an offline mode. In one embodiment, an event is identified when the Before Peak Test is satisfied.

Viewed from another aspect, the present invention provides a method for creating a database of Reference Property Vectors for use in analysing sensor data, including the steps of: (a) receiving a set of reference data; (b) identifying in the reference data a plurality of event stages; (c) processing the reference data in segments identified using a moving window having at least a dimension w by: extracting a plurality of properties used to populate a Reference Property Vector for each segment based on a corresponding event stage; allocating a segment type to each segment and associating the segment type with a corresponding Reference Property Vector; and shifting the window by X seconds; and (d) storing a set of Reference Property Vectors and corresponding segment types for use in analysing sensor data.

The moving window may have any closed regular or irregular polygonal shape such as square, triangular, hexagonal, quadrilateral or the like, or it may be e.g. round, oval or elliptical. The window sides may each have the same or different pre-defined dimensions. Alternatively, one or more of the window sides may have a dimension (e.g. length) which varies, e.g. depending on the type or property/properties of previous segment types in a sequence. In one embodiment, the window has only one dimension e.g. it represents a line having width w or height h or a line which is curved or diagonal but which does not form a closed boundary. A window dimension may alternatively be defined by trial and error. In a preferred embodiment, the moving window is a rectangle having a pre-defined height h and width w. Preferably, one of the properties is a sequence identifier representing the sequence number of an event that is detectable in the reference data.

Viewed from yet another aspect, the present invention provides a wetness event detection system for processing sensor signals to detect wetness events in sensor data obtained from one or more wetness sensors in a pad worn by a subject. The system includes (a) an input module configured to receive and optionally pre-process sensor data from the one or more wetness sensors; (b) a storage module configured to store reference wetness data; (c) processing means configured to process sensor data from the input module to identify wetness events in the sensor data; (d) a memory module storing instructions that are executable to cause the processor to perform a method of analysing sensor data; (e) a user interface configured to receive inputs from a user; and (f) a display means communicatively coupled with the processing means and configured to display wetness event information derived from the processing means. Preferably, memory module stores instructions that are executable to cause the processor to perform a method of analysing data using the method described above. The storage module may be located locally to other components of the system, or it may be positioned remotely and accessed e.g. via a communications infrastructure. Similar possibilities apply for the memory module. In this way, the inventive system may be deployed entirely or in part, in a cloud computing environment.

Viewed from another aspect still, the present invention provides a computer program comprising executable instructions readable by a processing means and causing the processing means to process incoming data, the instructions causing the processing means to perform steps including: (a) processing the incoming data in segments to output a sequence of segment types by extracting one or more properties of an incoming data segment to form an Unknown Property Vector for each segment of data in the incoming data; and (b) processing the sequence of segment types to identify events in the incoming data; wherein the sequence of segment types is determined, for each segment, by reference to a set of Reference Property Vectors that are relevant to the Unknown Property Vector.

Processing the incoming data in segments may involve applying a first function on the Unknown Property Vector and a set of Reference Property Vectors to identify at least a first subset of Reference Property Vectors that are relevant to the Unknown Property Vector. Optionally, a second function may be applied on at least a second subset of the Reference Property Vectors to determine a segment type for the Unknown Property Vector. Alternatively, processing the incoming data in segments may involve application of a logistic regression algorithm. The logistic regression algorithm may be generated offline using one or more candidate vectors that are created using a clustering and/or classification method applied to the complete set of Reference Property Vectors or a subset of Reference Property Vectors. The one or more candidate vectors contain elements representing a degree of belonging to each of a plurality of different segment types. In real time analysis the logistic regression algorithm identifies the segment type when applied to the incoming data.

Another aspect of the present invention provides a computer program comprising instructions readable by a processing means and causing the processing means to process incoming data, the instructions causing the processing means to perform steps including: (a) processing the incoming data in segments using a moving window to output a sequence of segment types; and (b) processing the sequence of segment types to identify events in the incoming data.

Viewed from another aspect, the present invention provides a computer program comprising instructions readable by a processing means and causing the processing means to process incoming data, the instructions causing the processing means to perform steps including: (a) receiving reference data; (b) identifying in the reference data a plurality of event stages; (c) processing the reference data in segments identified using a moving window having a dimension w, by: extracting a plurality of properties used to populate a Reference Property Vector for each segment; allocating a segment type to each segment and associating the segment type with a corresponding Reference Property Vector; and shifting the window by X seconds. The instructions also cause the processor to perform the step of (d) storing a set of Reference Property Vectors and corresponding segment types for use in analysing sensor data. Ideally, the reference data is smoothed before it is processed using the moving window, however in another embodiment it is possible to do segmentation without smoothing.

Viewed from yet another aspect, the present invention provides a computer program comprising executable instructions readable by a processing means and causing the processing means to process incoming data, the instructions causing the processing means to perform steps including: (a) processing reference data in segments identified using a moving window and identifying a segment type for each segment; and (b) associating the segment type with a plurality of properties for that segment.

The computer program may take any form, physical or non-physical, such as e.g. a product embodied in an optical, magnetic or electronic (e.g. USB) storage device, or embodied in a program product downloadable over a communication network such as the Internet.

Viewed from yet another aspect still, the present invention provides a method for analysing incoming data, comprising the steps of: (a) processing the incoming data in segments to output a sequence of segment types; and (b) processing the sequence of segment types to identify an event in the incoming data.

In one embodiment, the method includes storing one or both of a maximum and a minimum value obtained from a first group of samples in the incoming data, where one or both of the maximum and the minimum values are calculated as a function of a second group of samples in the incoming data; processing the first group of samples in the incoming data in segments to output a sequence of segment types, where the segment types are determined by comparing the incoming data in the first group of samples with at least one of the stored values; and processing the sequence of segment types to identify an event in the incoming data.

In another embodiment, the method includes storing one or more reference values from a first group of samples in the incoming data, where the one or more reference values are a function of the incoming data collected over a second group of samples; processing the first group of samples in the incoming data in segments to output a sequence of segment types, where the segment types are determined according to a relationship between a sequence identifier of the segment and one or more reference values; and processing the sequence of segment types to identify an event in the incoming data.

In another embodiment still, the method includes processing a first group of samples in the incoming data in one or more segments; determining one or more reference values for each segment, where the one or more reference values are determined as a function of incoming data comprised in each segment; processing the segments to output a sequence of segment types, where the segment types are determined according to a relationship between a sequence identifier in a segment and one or more reference values; and processing the sequence of segment types to identify an event in the incoming data.

In another embodiment still, the method includes processing a first group of samples in the incoming data in segments to output a sequence of segment types and one or more reference values where the one or more reference values are determined as a function of the incoming data in each segment, and each segment type in the sequence is determined by a relationship between a sequence identifier of the segment and one or more reference values; and processing the sequence of segment types to identify an event in the incoming data.

Throughout this specification, various processing steps are described and in some examples and embodiments discussed, the data and segments of data are referred to as being processed in sequence. It is to be understood, however, that the invention, in its broader application is not limited to sequential processing of data segments, or of windows of data, and that in many steps non-sequential data processing is contemplated though not always explicitly stated.

BRIEF DESCRIPTION OF THE DRAWINGS

The present invention will now be described in greater detail with reference to the accompanying drawings. It is to be understood that the embodiments shown are examples only and are not to be taken as limiting the scope of the invention as discussed herein and defined in the provisional claims appended hereto.

Tables 1 to 5 contain entries representing sets of Reference Property Vectors (RPV) that are progressively reduced in size during a process of determining a segment type for a segment of data represented in an Unknown Property Vector (UPV), according to an embodiment of the invention.

DETAILED DESCRIPTION OF THE INVENTION

According to an embodiment of the invention, a method for processing a stream of incoming data, particularly data from one or more wetness sensors, requires comparing property vectors obtained from the incoming data with a set of Reference Property Vectors obtained from historical or reference data.

Figure 1:
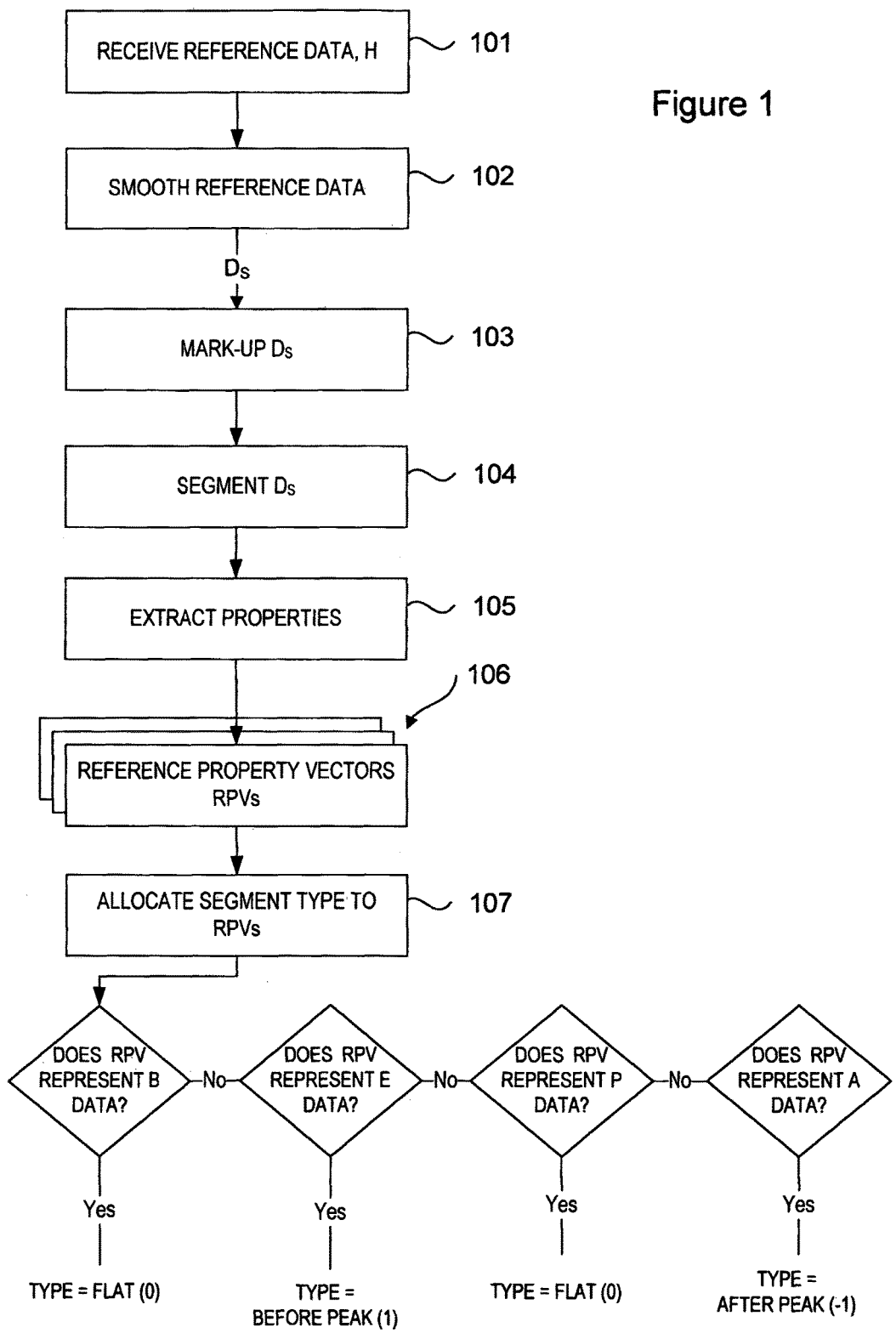
FIG. 1 is a flowchart showing steps in a method of generating a set of Reference Property Vectors each having an associated segment type, for use in an embodiment of the invention.

Referring firstly to FIG. 1, there is shown a method of generating a set of Reference Property Vectors for use with the present invention. In a step 101, reference data is received by a processing means which processes the reference data in such a way that a set of Reference Property Vectors 106 is obtained. Typically, the reference data is historical data obtained from one or more wetness sensors that have been used to sense urinary and/or faecal wetness events occurring in an absorbent article such as a pad. However, the sensors may alternatively/additionally sense other parameters such as temperature, pH, odour, gas, bioanalytes, pressure, movement, sound and the like. Alternatively/additionally, one or more of these other parameters may be utilised in the present invention e.g. by populating an element of one or more of the Reference Property Vectors used in the data analysis.

Ideally, the reference data is obtained for one or more pads and for a complete pad cycle. A pad cycle corresponds to a sequence of individual wetness events that occur during the wearing of a pad. As would be understood by the skilled addressee, a single wetness event does not necessarily cause the pad to reach its wetness absorbing capacity. Accordingly, sensor data for a complete "pad cycle" contains data corresponding to a number of individual wetness events in a sequence of events before the pad is changed (i.e. removed from the wearer and replaced with a fresh pad). Individual events in a pad cycle may be identified or referred to using an event sequence identifier. The event sequence identifier may be determined based on the number of events that have already been directed in a pad cycle.

In a preferred embodiment, reference data includes data obtained from more than one pad cycle observed for a particular subject. In a more preferred embodiment, the reference data includes data obtained from more than one pad cycle for a plurality of different subjects. The subjects may be indexed and/or grouped according to e.g. demographic indicators such as age, gender, health status, and the like. These demographic indicators may alternatively/additionally be used to populate an element in the Reference Property Vectors generated using the reference data, which vectors as discussed below.

Figure 4:
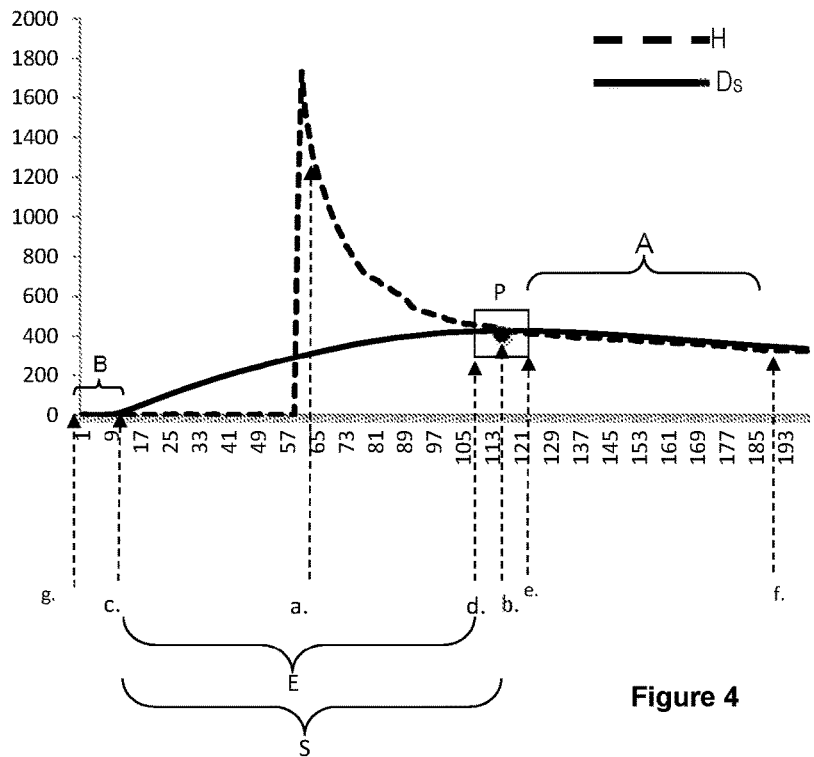
FIG. 4 is a schematic illustration representing reference data and smoothed reference data used to generate a set of Reference Property Vectors, according to an embodiment of the present invention.

FIG. 4 is a schematic illustration representing historical or reference data H corresponding to a wetness event. In a preferred embodiment, the local maxima in the unsmoothed reference data H representing the actual events are identified. Identifying the events in the unsmoothed reference data may be done using a manual marking up process by sight, or using an automated method. In some embodiments manual marking up is preferred because human oversight of the marking up process typically results in greater accuracy, particularly when the unsmoothed reference data contains artefact and spurious signal spikes that can intellectually be ruled out from comprising an "event peak", whereas an automated threshold detection approach may not be sufficiently sophisticated to make such distinctions.

In a preferred embodiment, the reference data H is smoothed in a step 102. Smoothing may be desirable to remove signal artefact and instabilities in the sensor signal. FIG. 4 also shows smoothed reference data $D_S$ derived from H. The smoothed data may be obtained using any suitable smoothing algorithm or formula. The smoothing algorithm typically uses a "smoothing window" which designates a section over which data is averaged in order to smooth the data values. Thus, the smoothing window may have a size S being the period over which data is averaged in order to achieve smoothed data output. The smoothing window size may be set statically or dynamically, and adjusted according to e.g. the sensor type used to obtain the reference data and/or the nature of the data and how much artefact or noise it contains. In one embodiment, the smoothing window size may be determined by trial and error.

As a result of smoothing the reference data, the location of various stages of wetness events represented in the data become shifted in time relative to the location marked up in the original (unsmoothed) reference data H. Accordingly, it is desirable in a step 103 to mark up the smoothed data. This involves identifying, in the smoothed reference data, data intervals that correspond with various stages of a wetness event in the unsmoothed reference data.

Typically, marking up the smoothed reference data, $D_S$, involves identifying the maximum value (corresponding to the event peak) and then working from there to identify the other event stages. Rising data values looking backward from the peak correspond to "Before Peak" event stage data. Decaying data values occurring after the peak can be identified as "After Peak" event stage data. The duration of this stage may be limited by a maximum decay period. Data occurring before the initial "Before Peak" event stage and occurring after an "After Peak" event stage but before a subsequent "Before Peak" event stage can be marked up as "Flat" event stage data. As the name suggests, "Flat" event stage data corresponds to event stages where there is little or no event activity of interest.

Thus, in an embodiment, the smoothed reference data $D_S$ is marked up so that the segments comprised in the smoothed reference data are associated with particular segment types, based on event stages as follows:

segments comprised in a "Flat" event stage are identified as "flat" segment types;

segments comprised in a "Before Peak" event stage are identified as "Before Peak" segment types;

segments comprised in a "Peak" event stage are identified as "flat" segment types; and segments comprised in an "After Peak" event stage are identified as "After Peak" segment types.

FIG. 4 has been marked up to identify these event stages. A "Flat" event stage is represented by smoothed data in section B. This corresponds to a sequence of smoothed data values which occur prior to the onset start of an event. The "Flat" event stage can be identified by looking for a flat section of smoothed data. An "After Peak" event stage is represented by smoothed data in section A and represents smoothed data values occurring after smoothed data values representing the "Peak" event stage. The decaying values from e. to f. represent "After Peak" event stage data A. This interval is limited by the length of a "Maximum Decay Period" (MDP) which may be set by trial and error, or as a function of previously processed data. The "Peak" event stage in the smoothed data is designated by the values inside the interval identified as P which is bounded in time by points d. and e. Point d. represents the end of a sequence of "Before Peak" event stage data Point e. represents the start of a period of "After Peak" event stage data. The interval from c. to d. represent "Before Peak" event stage data E.

Ideally, the step of marking up the smoothed reference data involves establishing a selection of key parameters from the data. In addition to identifying the points and intervals above, these may include but are not limited to:

Smoothing window size S being the period over which data is averaged in order to achieved smoothed data output;

Local maxima in the unsmoothed reference data represented at a;

A function N for transposing points in the unsmoothed reference data to smoothed reference data, where N is, in a preferred embodiment, configured according to the nature of the data and how much artefact or noise it contains. In one embodiment, the value determined by N is equivalent to the smoothing window size S and may be determined by trial and error. In another embodiment N is determined as a function of smoothing window size S. Corresponding maximum of the smoothed reference data represented at b $$\left(\text{where } b = a + \frac{N}{2}\right)$$

Slope orientation change point from "flat" to "Before Peak" event stage represented at c $$\left(\text{where } c = a - \frac{N}{2}\right);$$

Beginning point g. of "Flat" event stage represented at B (where g=c−B) and;

End point f. of the "After Peak" event stage (where f=b+A)

In a more generalized approach, a segment in an event stage may be represented by a vector having elements representing a degree of belonging or a probability to each of a plurality of different event stage types. In this approach instead of discrete transitions between stages being identified in the reference data, gradual changes may be designated. For example, event stage types may change gradually from Flat to Before Peak and from Before Peak to Flat from point a. to b., and c. to a. A linear, polynomial, sigmoid transition can be used for type transition between points a. to b.

In certain scenarios, special rules may be used for marking up the smoothed data. For example, two events may be combined if point c. in a current event happens before point e. of a previous event. Also, an event has no "Flat" event stage B if point c. in the current event occurs before point f. of the previous event. Where the time period between point f. of the previous event and point c. of the current event is less than B, then the "Flat" event stage commences only at point f. Additionally if there are segments of the data for which the identified events are nonsensical, then these areas are preferably marked as "unknown" so as to avoid contaminating the reference data.

Once the smoothed reference data has been marked up with event stages, it is processed in a step 104 to identify segments within the smoothed data which can then be labelled according to a "segment type". In one embodiment, the function used to process the smoothed data in this way may be referred to as a "Property Extractor Function" 105. Ideally, the outputs of the Property Extractor Function include a set of Reference Property Vectors 106 which are indexed or labelled according to their "segment type" (as determined by the Property Extractor Function). Thus, the "Property Extractor Function" may be applied to the smoothed data in finite segments, and the segments labelled according to when each segment occurs relative to the various event stages, based on the marked up smoothed data.

For example, the smoothed data may be represented at time $t^i$ by $S(t^i)$. The duration of the segment may be set to n units of time. According to an embodiment of the invention, a "Property Extractor Function" having notation f( ) may be represented as:

$$< P_1, P_2, \ldots, P_m \geq f(S(t^i), S(t^{i+1}), \ldots, S(t^{i+n}))$$

$$R^n \rightarrow R^m$$

Where P corresponds to the extracted properties making up the extracted Reference Property Vector for the segment and m corresponds to the number of elements in the property vector.

The focus (or window) of the Property Extractor Function is then shifted by an offset of $X_P$ units of time and the Property Extractor Function is applied on the next segment of smoothed reference data. The offset $X_P$ may be determined by any suitable method. This may involve trial and error to ascertain an appropriate trade-off between precision and usefulness of the extracted property vectors, and computational power required to obtain those vectors. In one embodiment, the offset $X_P$ corresponds to half the segment or window width. In an embodiment $X_P$ is variable and it is derived using a function applied to previously determined segment types (or segment type vectors). For example, if a consecutive sequence of segment types are identical for a long duration, it may be desirable to extend the length of $X_P$. An algorithm may, through learning, adapt a value for $X_P$ which is suitably based on previously processed data. Alternatively, $X_P$ may be a static value.

Dynamic determination of the value of $X_P$ may be desirable e.g. if the properties extracted from the moving window do not change much in a few consequent segments. This suggests that the sensor data is stable. In such cases, the offset $X_P$ may be increased thereby reducing the number of segments to be processed and so reducing the processing time or computational burden, thus increasing the performance of the system when performing segment typing or classification. Conversely if the changes between the properties extracted from the moving window are significant from segment to segment, then the offset $X_P$ may be decreased (or set to an initial or minimum value) to capture to a greater degree the changes represented in the data.

Determining a value for $X_P$ dynamically may also be useful for generating a balanced set of Reference Property Vectors. For example, it may be useful to compute the length of the Before Peak, peak, After Peak and unknown stages from the marked up and smoothed reference data and then set a smaller $X_P$ for the stages with shorter duration while setting a larger $X_P$ value for the stages with larger length. In case of having dynamic $X_P$, the value of $X_P$ is also recorded as one of the properties in each of segments.

Dynamic configuration of $X_P$ could increase the performance of the segment classification step 206 when bottom and/or top edges of the moving window are crossed many times by the sensor data. This could indicate that the data is noisy in that area and in this case, $X_P$ may be set to a larger value to avoid wasting computational effort on noisy segments of data.

Properties extracted and used to populate the property vectors (both Reference Property Vectors and Unknown Property Vectors discussed below) may include intrinsic properties and extrinsic properties. Intrinsic properties are properties which relate directly to the data contained within the window having focus. Extrinsic properties are not directly related to data within the window but may provide contextual information.

The properties for the Reference Property Vector may be extracted for a segment using any suitable means. Some of the properties may be identified manually. Alternatively/additionally, properties may be identified automatically by a processing means.

Example—"Property Extractor Function" Using Moving Window

The following section describes one example of an approach to extracting properties from data which employs a "moving window" approach to process reference data in finite segments. A moving window may be defined as a bounded window applied to data from which various 'properties' are extracted. The window may have any closed regular or irregular polygonal shape such as square, triangular, hexagonal, quadrilateral or the like, or it may be e.g. round, oval or elliptical. The window sides may each have the same or different pre-defined dimensions. Alternatively, one or more of the window sides may have a dimension, e.g. a length which varies, e.g. depending on the type or property/properties of previous segment types in a sequence. In one embodiment, the window has only one dimension e.g. it represents a line having width w or height h or a line which is curved or diagonal but which does not form a closed boundary. A window side length may alternatively be defined by trial and error.

In a preferred embodiment, the moving window is a rectangle having a pre-defined height h and width w. Ideally, height h is proportional to a voltage range embodied in the sensor data while the width w is proportional to a period of time. The inventors have found that a value for w which produces useful results is 20 seconds although window widths as short as 0.1 seconds or 0.5 seconds or 1 second or 10 seconds or e.g. 15 seconds may be useful. Similarly, window widths of longer than 20 seconds, e.g. 30 seconds, 40 seconds, 50 seconds, 60 seconds, 120 seconds, 180 seconds or even longer may be useful. A typical h value is in the order of e.g. 0.5% to 15% of maximum signal voltage, or bounded by about 10% of maximum signal voltage or even say 1%, 3% or 5% of maximum signal voltage may define h. Width w typically corresponds to the segment duration n referred to above.

Alternatively w and/or h may be determined dynamically to reduce the processing time for segment classification and/or to create a balanced set of Reference Property Vectors (see discussion of $X_P$ above). For example, if the top and bottom edges of the moving window are not crossed by sensor data then it could be deduced that the moving window is currently focussed on a flat section of data so the window width w may be increased. Width w of the window may be decreased when the sensor data intersects with the top and bottom edges of the moving window.

In another case, if there are many data intersections on the top and/or bottom edges of the moving window (which may imply that the data is noisy in that segment) then the height h and the width w of the moving window could be increased to capture the trend of data set appropriately which may increase the performance of the segment classification step 206. If h and w are set dynamically, then both values of h and w may be recorded as properties of each segment.

Each Moving Window is defined by a reference point $R^i(T,V)$ in the smoothed data such that the moving window comprises any sensor data R(T,V) where T, and V are $$t^i - \frac{w}{z} < T < t^i + \frac{w}{\left(\frac{z}{z-1}\right)} \text{ and } v^i - \frac{h}{z} < V < v^i + \frac{h}{\left(\frac{z}{z-1}\right)}, z = (0 + \infty),$$

where t is time;
w is window width;
z defines where the window's centre is located;
$v^i$ is voltage value of the signal at time i
$t^i$ is the time at i The moving window is ideally centred on a reference point $R^i$ (z=2) although this reference point need not be the "centre" of the window. Once properties are extracted for the segment of data within the window, the moving window is shifted by an offset of $X_P$. The size of the offset $X_P$ influences the quantisation of the segments for which the properties are extracted. This in turn affects processing speed and efficiency. For instance, if $X_P$ is half w, then there may be slower processing since adjacent windows overlap by 50% but there may be greater accuracy in the analysis which follows. There is a trade-off between speed and quality of the vectors obtained by shifting the window along in increments which are too large. Ideally, the offset $X_P$ is no longer than w, although ideally there is some overlap between adjacent windows or "segments" for which properties are extracted.

Figure 5:
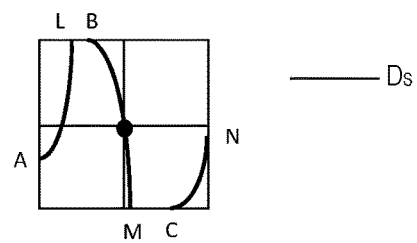
FIG. 5 represents a moving window applied to a segment of smoothed data according to an embodiment of the present invention.

FIG. 5 represents a moving window applied to a segment of smoothed reference data $D_S$. The number of intersections with the window boundaries in FIG. 5 indicate that the $D_S$ is a relatively noisy signal. In one embodiment, intrinsic properties (extracted using the Property Extractor Function) include e.g. the number of data samples in an edge of a moving window; the entry point on signal entry sides of the window and the exit point on signal exiting sides of the window. Entry and exit points may be quantified or described by reference to e.g. x and y coordinates of the sensor data, having respect to axes that can be applied to the window. Another way to quantify the entry and exit points is to calculate the distance between them (e.g. the distance between A and N in FIG. 5). Alternatively, entry and exit points may be quantified e.g. by a function calculating a distance between one or more reference points in the window (or on its boundaries) and the entry point and exit point.

Extrinsic properties typically include information which relates the data within the window to other segments in the data stream, which stream normally represents a number of events occurring over a period of minutes, hours, days or even longer. For example, extrinsic properties (extracted using the Property Extractor Function) may include a sequence identifier for the window, which gives context to whether a segment represents event data for a first event in a sequence of events in a pad cycle, or say a second or third event in the cycle. Alternatively/additionally extrinsic properties may include e.g. a previous maximum value of data encountered by the moving window; a duration representing the time elapsed since the start of the data stream (e.g. the start point, in time, of the window for that segment relative to the start point of the data set); time elapsed since a previous event peak in the data stream, or the like.

The properties may be extracted for a segment (identified by the moving window) using any suitable means. Some of the properties for the Reference Property Vector may be identified manually. Alternatively/additionally, properties may be identified automatically using processing means configured to apply one or more functions that extract the properties as the moving window passes over or propagates across the stream of data.

It is also contemplated that properties ascribed to a segment inspected using a moving window may include e.g. demographic information such as e.g. subject age, gender, weight, mobility, cognitive function etc, observational data pertaining to the period over which the sensor data is obtained (e.g. meal and fluid intake, toileting events etc) and other information such as movement, temperature, pressure and the like. These may include extrinsic and intrinsic properties.

FIG. 5 represents a moving window applied to a segment of smoothed data $D_S$ and from which the following properties have been obtained:

| Intrinsic properties | |
| --- | --- |
| Window size w = 10 sec; h = 0.1v | |
| Number entry points on left side | 1 |
| Number entry/exit points on top side | 2 |
| Number entry/exit points on bottom side | 2 |
| Number entry points on right side | 1 |
| Point A (entry): | −0.2 |
| Point B (entry): | 0.8 |
| Point C (entry): | −1.3 |
| Point L (exit): | 1.3 |
| Point M (exit): | −0.95 |
| Point N (exit): | −0.1 |
| Segment type: | 1 (Before Peak) |
| Extrinsic properties | |
| Event Number: | 2 |
| Previous max value: | 200 |
| Time since last event: | 650 |
| Moving Speed: | 1 |

Figure 6A:
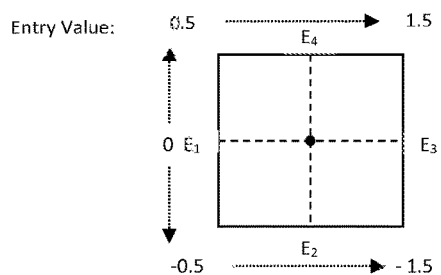
FIGS. 6a and 6b represent schema for attributing values to window entrance and/or exit properties according to an embodiment of the present invention.
Figure 6B:
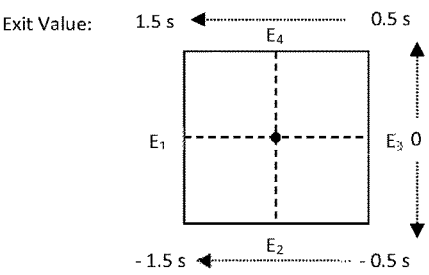

The entry and exit values may be quantified or identified in any suitable manner. In this example, they have been quantified using the schema identified in FIGS. 6a and 6b. FIGS. 6a and 6b represent schema for attributing values to window entry and/or exit properties.

One of the intrinsic properties identified above is "segment type" which is designated as "1" or "Before Peak". This is determined in a step 107 and in one embodiment, involves automatic and/or manual inspection of the smoothed reference data in which the segment is located, using the parameters discussed in relation to FIG. 4. Alternatively/additionally, manual inspection may be used to calibrate the result from an automatic inspection process or to identify noise in the smoothed data. In an embodiment, there are 3 segment types identified as follows:

| Segment type | Segment type ID |
| --- | --- |
| Flat ("B" data) | 0 |
| Before Peak ("E" data) | 1 |
| After Peak ("A" data) | −1 |

Optionally, there may be a fourth segment type known as:

| Segment type | Segment type ID |
| --- | --- |
| Unknown | 0 (null) |

Segments having type "unknown" are typically those segments in which the smoothed data corresponds noise or artefact, and for which a null or zero value is ascribed to minimise the adverse effect of those segments on the data analysis.

Each of the intrinsic and extrinsic properties forms an element of a Reference Property Vector extracted for the segment over which the window is positioned. The segment type may occupy an element of the Reference Property Vector, or may be associated with the Reference Property Vector in some other way. After the moving window has propagated across the reference data, and the properties extracted, a set of Reference Property Vectors 106 can be obtained. It is to be understood that the moving window need not propagate across the sensor data in chronological sequence. Alternatively, windows or segments may be extracted out of sequence or at random, and the Reference Property Vectors populated or determined out of sequence also.

Once the set of Reference Property Vectors 106 has been established from the reference data, it can be used in a process of analysing incoming data from sensors. Ideally those sensors are wetness sensors, for detecting wetness events in pads worn by incontinent subjects. The Reference Property Vectors may be obtained once and then used and re-used as necessary to analyse wetness sensor data to identify wetness events. There may be different sets of Reference Property Vectors obtained for use in different analysis scenarios. For example, one set of Reference Property Vectors may be used to analyse wetness sensor data from incontinent adult subjects, whereas a different set of Reference Property Vectors may be used to analyse wetness sensor data from incontinent babies, or children. Similarly, different sets of Reference Property Vectors may be used to analyse sensor data from different sensor types.

The term "Reference Property Vectors" is used herein to designate a set of segment properties for reference data. It is not to be limited to data represented as "vectors" as such. That is, the term Reference Property Vectors is to be taken as a reference to the reference data and properties that may be extracted from that data in segments, or as a reference to e.g. a look up table or the like in which properties extracted from the data are represented.

Figure 2:
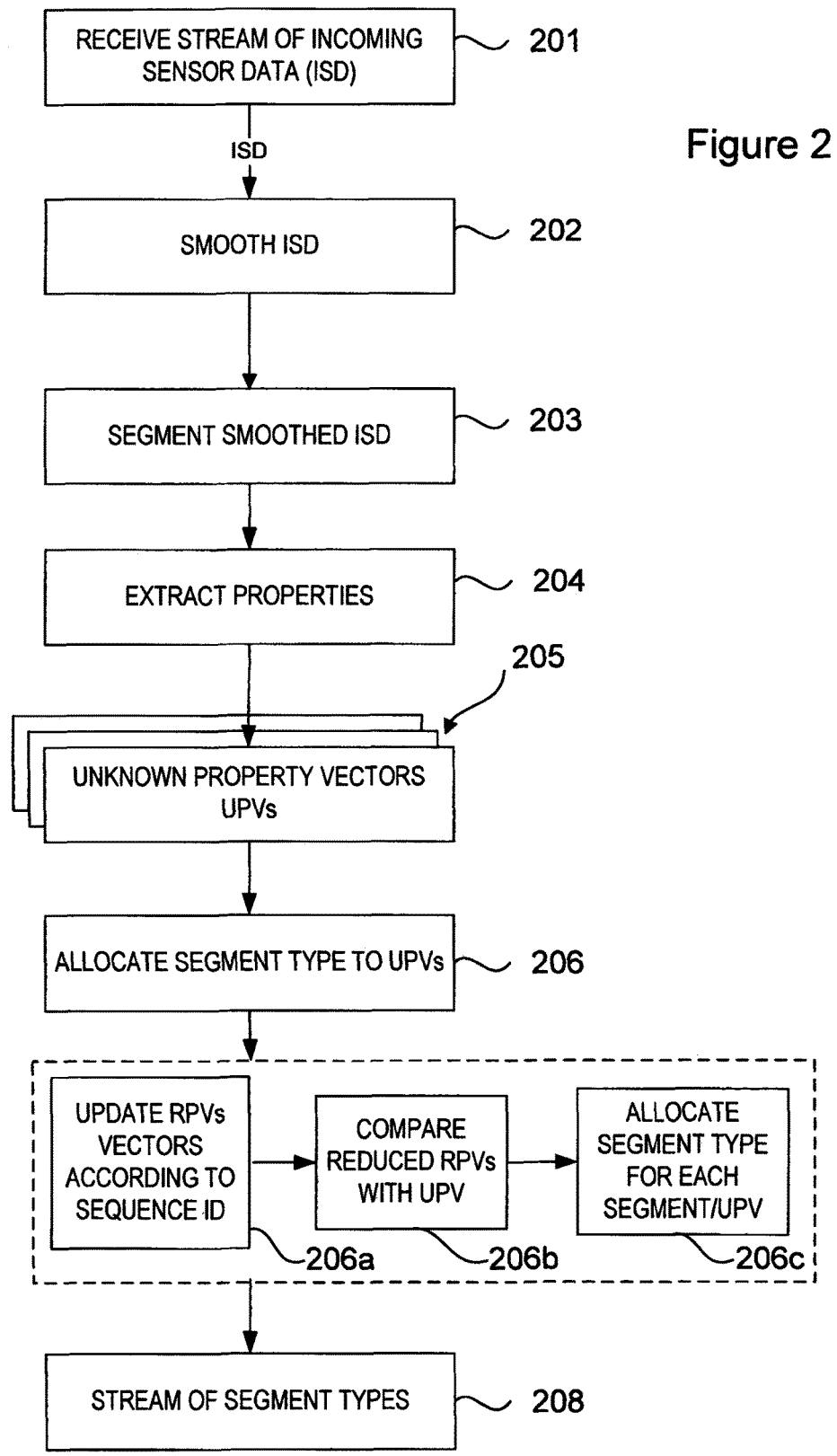
FIG. 2 is a flowchart showing steps in a method of determining segment type for a plurality of segments in a stream of incoming data, according to an embodiment of the invention.

Referring now to FIG. 2, there is a flow chart showing steps in a method of determining segment type for a plurality of segments in a stream of incoming data from a sensor, according to an embodiment of the invention. In a step 201, a stream of incoming sensor data (ISD) from one or more sensors (e.g. wetness sensors) is received. Preferably, the incoming sensor data is smoothed in a step 202, using a smoothing algorithm or smoothing function. Smoothing of incoming data may be achieved in a manner similar to smoothing described in relation to the reference data discussed above.

In a step 203, the smoothed incoming data is segmented, and properties are extracted in a step 204. However in an embodiment the incoming data can be segmented and its properties can be extracted without being smoothed. Ideally, segmentation of the smoothed incoming data is done using a moving window method of the kind described above in connection with the Property Extractor Function utilised for segmenting and extracting properties for the smoothed reference data. The output of segmenting in step 203 and property extraction step 204 is conceptually referred to as a set of Unknown Property Vectors 205.

In a preferred embodiment, the same constraints of the moving window applied to the smoothed reference data may apply to the smoothed incoming data. Thus, the same moving window size may be used (having width w and height h) and the same window offset $X_P$ may be used to segment the smoothed incoming data. Ideally, this is done substantially in real time although post-processing may be useful in certain circumstances. Once the smoothed incoming data has been segmented and the properties extracted, it becomes necessary to determine the "segment type" for each of the segments in the smoothed data set. Segmenting of incoming data and determining the properties of that data need not be done in a sequential (chronological) order in which the segments appear. The segments may be obtained and properties ascribed in a non-sequential or random order. However sequential processing may, in certain embodiments, give better computational efficiency. While the segment type may be manually determined for each of the segments in the smoothed reference data, that is laborious and not practically viable for processing large volumes of incoming data for use in real time analysis of wetness sensor signals obtained for a plurality of incontinent subjects.

Accordingly, an automated method step or group of steps 206 is used to determine the "type" for each of the segments in the smoothed incoming data and represented in the set of Unknown Property Vectors 205. Many different approaches may be adopted here. Any function capable of determining segment type (a response variable) from the relationship or relevance between the Unknown Property Vector entries for a segment and the Reference Property Vectors (explanatory variables) may be employed. The function may be determined using a range of methods such as, for example, regression analysis or other classification methods such as Support Vector Machine algorithms (SVM), Decision Trees, K-nearest neighbours (K-NN) and the like. Other methods or functions may be utilised as may be recognised as suitable to one of skill in the art. These may include, for example, neural network algorithms, clustering and other functions capable of determining relationships. A "sort" function may then be applied on each of the segments represented in the set of Unknown Property Vectors 205 to obtain the relevant segment "type" for each of the segments in the smoothed incoming data.

In general terms, one approach to determining the relationship which maps segments represented by Unknown Property Vectors and segments represented by Reference Property Vectors is illustrated in FIG. 2 which shows, the step of updating the set of Reference Property Vectors involved in the analysis according to sequence ID at 206a. Reference Property Vectors having a different sequence identifier to the sequence identifier of the Unknown Property Vector are eliminated, which produces a reduced set of Reference Property Vectors. In another embodiment of step 206a, Reference Property Vectors are weighted according to their sequence identifier, and how relevant each sequence identifier is to the Unknown Property Vector. If the weighting is set to one for all vectors in the set of Reference Property Vectors (e.g. when the Sequence ID of the Reference Property Vector is the same as the Sequence ID of the Unknown Property Vector) then all the Reference Property Vectors are kept and so the reduced set of Reference Property Vectors is the same as the original set of Reference Property Vectors. In most cases however, the set of Reference Property Vectors will contain segments with different Sequence IDs. Those which have a closer relationship to the Sequence ID of the Unknown Property Vector may be given a higher weighting (or relevance ranking) than those having disparate Sequence IDs.

For example, for an Unknown Property Vector having Sequence ID=3, any Reference Property Vector also having Sequence ID=3 is allocated a weighting=1. Reference Property Vectors having a Sequence ID=2 or 4 may be allocated a weighting of 0.5 whereas Reference Property Vectors having e.g. Sequence ID=1 or 6 may be allocated a weighting of zero. Any Reference Property Vectors having a weighting of zero are excluded from consideration whereas the influence of the remaining vectors is modified in accordance with their weighting. This may be achieved using one or more functions.

In a step 206b the Unknown Property Vector from 205 is compared with the reduced set of Reference Property Vectors (RPVs) and in a step 206c the most common or relevant segment type represented in the reduced set of Reference Property Vectors is allocated to the Unknown Property Vector for the segment having the focus of the moving window. A more detailed outline of such a method is described in relation to the "Segment Classifier Function" exemplified below.

The segment type may be ascertained or classified using a deterministic or a non-deterministic approach in step 206. Using a deterministic approach, a segment may be attributed a single "segment type" based on e.g. the most commonly occurring segment type in the Reference Property Vectors having greatest similarity or relevance to the segment represented by the Unknown Property Vector. Yet in a more general approach, each segment type is represented by a segment type vector which represents the probability or likelihood of belonging of that segment to each of the segment types available. In one embodiment, a Segment Classifier Function a( ) used for non-deterministic determination or classification of segment type, may be represented mathematically as:

$$(T_1^n, \ldots, T_i^n, \ldots, T_k^n) = a(p_1^n, \ldots, p_i^n, \ldots, p_m^n, T_1^{n-1}, \ldots, T_i^{n-1}, \ldots, T_k^{n-1})$$
$$R^m \rightarrow R^k$$

or in another version as:

$$(T_1^n, \ldots, T_i^n, \ldots, T_k^n) = a(p_1^n, \ldots, p_i^n, \ldots, p_m^n)$$
$$R^m \rightarrow R^k$$

where k is the number of different segment types available for attribution to a segment. $T_i^n$ is the likelihood that the segment n, which is represented by $$(p_1^n, \ldots, p_i^n, \ldots, p_m^n),$$

belongs to segment type i, and populates each element of a segment type vector $$(T_1^n, \ldots, T_i^n, \ldots, T_k^n).$$

Example "Segment Classifier Function"

The following section describes two examples for determining segment type (segment type vector) for smoothed incoming sensor data by utilization of a K-NN algorithm and logistic regression, based on Reference Property Vectors extracted from smoothed reference data. This may be referred to as a "Segment Classifier Function" represented in FIG. 2 at step 206. However it is to be understood that any function capable of determining relationships may be suitable for classifying segments; the invention is not limited to a K-NN algorithm or logistic regression.

In one embodiment, each Unknown Property Vector has property elements corresponding to e.g. event sequence identifier; peak value of the previous event; time since last event; intrinsic window properties; and also an indicator of segment type. The indicator of segment type may be represented by a value (or a segment type vector of values) and is determined by the Segment Classifier Function. The event sequence identifier indicates the sequence order of the segment as it relates to a sequence of wetness events in a pad cycle. For instance, if the segment corresponds to a first wetness event in the pad cycle then the event sequence identifier is 1; if the segment corresponds to a second wetness event in the pad cycle then the event sequence identifier is 2, if the segment corresponds to a third wetness event in the pad cycle then the event sequence identifier is 3, and so on.

In an embodiment for determining the segment type, the Segment Classifier Function excludes from consideration those Reference Property Vectors having an event sequence identifier which is different to the event sequence identifier of the Unknown Property Vector. This may be used to produce a reduced set of Reference Property Vectors. In another embodiment the classifier function considers all the Reference Property Vectors. It is to be noted that although it may be conceptually helpful to have regard to a "reduced set" of Reference Property Vectors, physically producing such a reduced set (e.g. in memory of a computer or otherwise) may not be necessary. For example, if the event sequence identifier of the Unknown Property Vector is "2" then all of the Reference Property Vectors with an event sequence identifier other than "2" are merely disregarded in the processing steps, without physically producing a reduced set of Reference Property Vectors. Weighting may also be used. However having the relevant Reference Property Vectors separated in different tables increases the speed of segment type classification as the processing means does not need to compare the sequence identifier of the Unknown Property Vector with every single sequence identifier in the set of Reference Property Vectors.

Table 1 represents a set of Reference Property Vectors. Table 2 represents a "reduced set" of Reference Property Vectors in which vectors corresponding to reference data segments having an event sequence identifier other than 2 have been removed. In each table, x is a mask which, for the sake of simplicity, has been used to replace actual values.

In some embodiments, Table 2 may be sufficient to identify type "1" (i.e. "Before Peak") as the segment type attributable to the Unknown Property Vector since it is the most commonly occurring in the reduced set of Reference Property Vectors presented in Table 2. However such an approach produces rudimentary results. In a preferred embodiment, with a K-NN algorithm the Segment Classifier Function compares the Unknown Property Vector to the reduced set of Reference Property Vectors. Ideally the comparison is a distance function e.g. Euclidian distance which measures the distance between the Unknown Property Vector, and each of the vectors in the reduced set of Reference Property Vectors.

Another embodiment uses a logistic regression algorithm to determine segment types for incoming data. The complete set or a reduced set of Reference Property Vectors may be used to derive the logistic regression algorithm in which the output represents the probability of a segment being one or more of After Peak, Before Peak, Flat or Unknown. The logistic regression algorithm may be generated using e.g. clustering or classification methods which group the reduced set or the complete set of the Reference Property Vectors into a number of classes or clusters, where each class or cluster can be represented by one or more chosen candidates. The segment type of the chosen candidate/s represents the frequency of each segment type occurring in that class/cluster which in turn, represents a probability of the class/cluster being of the type "After Peak", "Before Peak", "Flat" or "Unknown". One or more candidates representing a cluster or a class can be chosen to indicate the probability of the segment being of a particular type, the selection being based on one or more of: centre of the cluster or class, an average of the vectors in the cluster or class, a distance or similarity of each vector in the cluster or class to the representative candidate/s. The set of selected candidates and their probabilities may then used to derive the logistic regression function.

The logistic regression function can be applied to a set of Unknown Property Vectors to estimate the probability of a segment of incoming data being one or more of "After Peak", "Before Peak", "Unknown" or "Flat". In another embodiment a plurality of logistic regression models can be applied; where each model is chosen based on the similarity between the Unknown Property Vector and a class/cluster i.e. in an ensemble manner.

In an embodiment which utilizes a K-NN algorithm, the distance function may be computed by applying functions $u_i(\ )$ on the distances between each of the properties in two vectors being compared, giving rise to dist( ) and yet another function h( ) is applied on the set of the functions $u_i(\ )$ to compute a value representing the distance. Following is mathematical formulation for computing a distance for two vectors $$\vec{x} = \langle x_1, x_2, \ldots, x_n \rangle$$

and $$\vec{y} = \langle y_1, y_2, \ldots, y_n \rangle$$

$$h(u_1(dist(\vec{x}, \vec{y}, 1)), u_2(dist(\vec{x}, \vec{y}, 2)), \ldots, u_n(dist(\vec{x}, \vec{y}, n)))$$

where dist( ) is a function to compute the distance between two vectors for a property, and $u_i(\ )$ and h( ) are any types of functions that can determine relationships. In an embodiment the selection of dist and $u_i(\ )$ and h( ) involves trial and error.

In one example, the calculated value is the distance between "peak value of the previous event" and "length from previous peak". Table 3 contains a reduced set of reference property values from Table 2 with Euclidian distances, as calculated for each of the vectors in the reduced set, appended in the right column. Ideally, the entries in the further reduced set of Reference Property Vectors from Table 3 are then sorted in order of increasing Euclidian distance, as represented in Table 4.

In one embodiment, according to the K-NN method, the vectors in the further reduced set of Reference Property Vectors corresponding to Table 4 are again further reduced by removing the vectors with a Euclidian distance greater than $\epsilon 1$. In yet another embodiment, Table 4 is further reduced by removing the last n % vectors with largest distances. This results in elimination of some of the Reference Property Vectors which are not similar to the Unknown Property Vector and so to keep only the most "relevant Reference Property Vectors" as represented in Table 4. The most relevant Reference Property Vectors may be referred to as the k-nearest neighbours. In yet another embodiment none of the Reference Property Vectors are eliminated and so in this case the reduced set of Reference Property Vectors is the same as the original set of Reference Property Vectors with an extra field added representing the relevancy ratio of each Reference Property Vector to the Unknown Property Vector.

In an embodiment, a hierarchical elimination may be applied where a second Euclidian distance is calculated for a plurality of selected properties from the segment represented by the Unknown Property Vector and also for the corresponding properties in the k-nearest neighbours of the reduced set of Reference Property Vectors. Again, the entries are sorted according to the computed distance and referred to as "second k-nearest neighbours".

The last m % of the sorted distances in the second k-nearest neighbours set are eliminated from consideration. Typically, m is defined by trial and error. Alternatively, the last rows of a table representing the second k-nearest neighbours or the neighbours with distance m % greater than $\epsilon2$ are removed from the "second k-nearest neighbours" set to produce a set of "reduced second k-nearest neighbours". In an embodiment, the majority of the segment types in the "reduced second k-nearest neighbours" is then selected as the appropriate segment type to be ascribed to the Unknown Property Vector. In another embodiment, in addition to the type of vectors in the "reduced second k-nearest neighbours", the distance value of each vector is taken into account as the weight (importance) of the that vector's type.

The number of occurrences of each segment type in the reduced second k-nearest neighbours may be referred to as a number of votes. Where the number of votes for each segment type produces a result in which more than one segment type has a majority, then the type may be re-ascertained by changing the values of one or more of n or m or $\epsilon1$, or $\epsilon2$, or deciding on or influencing the type for the Unknown Property Vector vote based on the segment types determined for the previous segment; or applying a different distance function in step $206b$. It is to be understood that the value of n or m or $\epsilon1$ or $\epsilon2$ may be determined using any suitable method. In an embodiment, their selection involves trial and error. The values of these variables may be static or dynamic.

In certain embodiments, it is desirable to avoid a situation where the probability or number of votes for all of the segment types is substantially similar. That is, it may be desirable to avoid a situation where there is no segment type (or sequence of segment types) which is more prevalent than the others, e.g. a scenario where all the segment types have a probability of 0.25. To adjust for this, the threshold value of one or more of n or m or $\epsilon1$ or $\epsilon z$ may be determined dynamically. Ideally the values are determined in such a way that the probability changes between adjacent segments in a sequence are gradual. An example demonstrating gradual variation in segment type probability is shown below:

| | Segment number | | | | | | | | |
|---|---|---|---|---|---|---|---|---|---|
| | i | i+1 | i+2 | i+3 | i+4 | i+5 | i+6 | i+7 | i+8 |
| Before Peak probability | 90% | 80% | 70% | 50% | 30% | 20% | 10% | 10% | 5% |
| After Peak probability | 10% | 20% | 30% | 50% | 70% | 80% | 90% | 90% | 95% |

The outcome of the segment type allocation for the complete set of smoothed incoming data is a stream of segment types 208 which are then used in an analysis process. In another embodiment, the outcome of the segment type allocation is a stream of segment-type vectors.

Correcting Imbalances in Reference Property Vector Segment Types

In one embodiment, the set of Reference Property Vectors used to determine the type of each segment in the smoothed incoming data may be unevenly balanced. This may occur e.g. as a result of smoothing or having many pad cycles in the reference data which contain no events. That is, the set of Reference Property Vectors contains many of one segment type but few of another type. In an embodiment, to avoid domination of the analysis by segment types which appear more frequently, the types which have fewer occurrences may be multiplied in the reference data set until the number of segment types are evenly balanced In another embodiment and for probabilistically determined segment-type vectors, votes utilised in the segment allocation step 206 may be weighted according to the number of occurrences of a particular segment type in the complete set of Reference Property Vectors. For example, if in the set of Reference Property Vectors the proportion of "Before Peak" segment types is double that of "Flat" segment types, then the likelihood that an incoming data segment is of type "Before Peak" should be halved in step 206. Other approaches may be adopted to account for unevenness in the segment type spread in the set of Reference Property Vectors.

Processing a Stream of Segment Types

Figure 3:
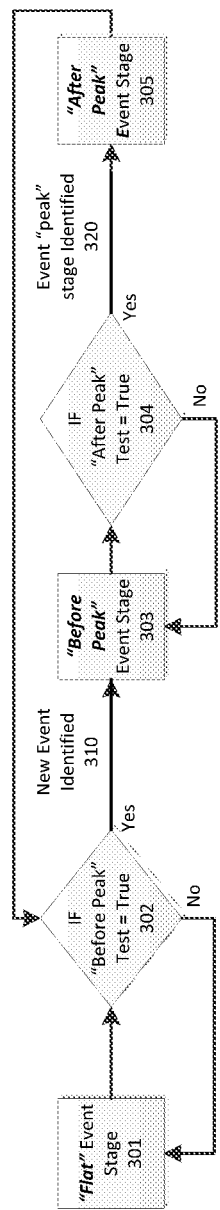
FIG. 3 is a state transition diagram for identifying wetness events in a stream of incoming data according to an embodiment of the present invention.

FIG. 3 is a state transition diagram representing steps in a method of processing a stream of segment types 208, to analyse the incoming data and then detecting an event. This processing occurs subsequent to the application of the segment classifier function to allocate segment types to a sequence of smoothed incoming data. An objective of the analysis is to detect events in the data and to this purpose, identify for a particular sequence of incoming data, the corresponding stage of an event, where stages are typically selected from the group including a "Flat" stage, a "Before Peak" stage, an optional "Peak" stage and an "After Peak" stage. Typically, it is assumed that incoming data prior to an event begins with a "Flat" stage at 301. At 302, a test is executed to determine if the sequence of segment types satisfies a "Before Peak" test. If the Before Peak Test is satisfied, then the event stage is deemed to be "Before Peak" at 303. The commencement of a "Before Peak" stage at 303 makes it possible to identify the start of a new wetness event in the pad cycle at 310. If the "Before Peak" test at 302 is not satisfied then the "Flat" event stage at 301 continues.

At 304, a test is executed to determine if the sequence of segment types satisfies an "After Peak" test. If the "After Peak" test is not satisfied, then the "Before Peak" event stage at 303 is deemed still to be current. If the "After Peak" Test is satisfied at 305, then it is possible to determine or infer the "peak" stage of the event in further processing, at 320. Subsequent to that, if a "Before Peak" test is satisfied, then the event stage is deemed to be "Before Peak" at 303. Alternatively, the "After Peak" event stage at 305 is deemed to be still current.

The Before Peak Test and After Peak Test may each be implemented in any suitable manner. In one embodiment, where the segment type is determined for each Unknown Property Vector using a segment type value, the Before Peak Test and After Peak Test may implemented as outlined in Tests A and C (below). In another embodiment, where the segment type is determined for each Unknown Property Vector using segment type vector (comprising a plurality of segment type values), the Before Peak and After Peak Tests may be implemented as outlined in Test B.1, B.2 and C In another embodiment, outlined in Test C, α, β, and l are set by applying functions k( ), l( ), and g( ) on a previous sequence of segment types or a previous sequence of segment type vectors. Determining the functions k( ), l( ) and g( ) may involve trial and error, or applying an optimization method to seek values or functions for k( ), l( ), and g( ) such that the performance of the event detection is maximized. In yet another embodiment k( ) and 10 may derive α%, and β%, as exemplified in Tests B.1 and B.2.

Test A
1. Set two thresholds, α and β, to be used in the Before Peak and After Peak tests respectively.
2. Set test size, l.
3. For each segment type in the stream of segment types 208, determine the sum of the previous l segments and store the value in T such that
   If $T \geq \alpha$,
      Before Peak Test=TRUE
   Else if $T \leq \beta$,
      After Peak Test=TRUE
4. An event peak stage is represented by the sequence of segment types following a "Before Peak" stage, and prior to the After Peak stage, where $\alpha > T > \beta$.

Application of Test A is shown in Example A.

Example A

Showing application of Before Peak and After Peak Test A.
Assume a stream of segment types:
   0,0,0,0,1,1,1,0,−1,null,1,1,1,1,1,1,null,0,−1,−1,−1,0,null, 1,1,−1,−1,−1,0,0
Where null can be attributed a segment type value=0.
Test size l=5
Before Peak threshold α=3
After Peak threshold β=−2
The stream of values T is:

| $1^{st}$ | $2^{nd}$ | $3^{rd}$ | $4^{th}$ | $5^{th}$ | $6^{th}$ | $7^{th}$ | $8^{th}$ | $9^{th}$ | $10^{th}$ | $11^{th}$ | $12^{th}$ | $13^{th}$ | $14^{th}$ | $15^{th}$ | $16^{th}$ |
|---|---|---|---|---|---|---|---|---|---|---|---|---|---|---|---|
| 1 | 2 | <u>3</u> | 3 | 2 | 1 | 1 | 1 | 2 | 4 | 5 | 5 | 4 | 3 | <u>1</u> | <u>−1</u> |

| $17^{th}$ | $18^{th}$ | $19^{th}$ | $20^{th}$ | $21^{st}$ | $22^{nd}$ | $23^{rd}$ | $24^{th}$ | $25^{th}$ | $26^{th}$ | $27^{th}$ | $28^{th}$ |
|---|---|---|---|---|---|---|---|---|---|---|---|
| <u>−3</u> | −3 | −3 | −1 | 1 | 1 | 0 | −1 | −2 | −3 | −2 | −1 |

Test A reveals a positive Before Peak Test (signifying start of a new event) at the third value i.e. T=3 (underlined) and a positive After Peak Test (signifying end of peak stage and start of after event) at the 17th value i.e. at T=−3 (underlined). An event peak is represented by the data corresponding to 3>T>−2. Accordingly the event peak is represented by data corresponding to the $15^{th}$ and 16th values of T having values 1 and −1 respectively (shown with double underline).

Test B.1
1. Set two thresholds, α% and β%, to be used in the Before Peak and After Peak tests respectively.
2. For each Unknown Property Vector, identify the segment type in the segment-type vector having the highest likelihood of belonging.
3. For each segment type in the stream of segment-type vectors:
   if the segment type with highest likelihood of belonging is "Before Peak"
   and
   the likelihood is >α%,
      Before Peak Test=TRUE
      Define one event.
   if the event type with the maximum highest likelihood of belonging is "After Peak"
   and
   the likelihood is >β%,
      After Peak test=TRUE
4. An event peak stage is identified as the data values in the smoothed incoming data represented between the start of the "Before Peak" stage and the start of the "After Peak" stage.

Test B.2
A variation of Test B.1 that varies Step 3:
3. For each segment type in the stream of segment-type vectors:
   If the Before Peak type is >α%,
      Before Peak Test=TRUE
      Define one event.
   and
   If the After Peak type is >β%,
      After Peak test=TRUE An application of Test B.1 is shown in Example B.1.

Example B.1

Assume a stream of segment-type vectors where the segment types in each vector having the highest likelihood of belonging are as follows, where f represents flat, r represents Before Peak, n represents null and d represents After Peak segment types:
   f 30%, r 50%, r 89%, n 90%, f 95%, r 30%, d 10%, d 30%, r 20%, d 70%, f 20%, d 50%
Threshold α=80
Threshold β=50

Test B.1 reveals a positive Before Peak Test (signifying start of a new event) in data represented by the 3rd segment (where r=89%) in the sequence of segments obtained from the incoming data. Similarly, Test B.1 reveals a positive After Peak Test (signifying end of peak stage and start of after event) at the 10th segment (where d=70%).

Test C
(a) Set two variable thresholds α and β, which are derived by applying functions k( ) and l( ) on the previous segment types (or segment type vectors), to be used in the Before Peak and After Peak tests respectively
(b) Set variable test size l by applying g( ) on previous segment types (or segment type vectors)
(c) For each segment type (or segment type vector) in the stream of segment types 208, apply z( ) on the previous l segments and store the value in T such that
   If $T \geq \alpha$,
      Before Peak Test=TRUE
   Else if $T \leq \beta$,
      After Peak Test=TRUE (d) An event peak stage is represented by the sequence of segment types after Before Peak and prior to the After Peak values where $\alpha > T > \beta$.

In Test C, the output of applying z( ) on the previous l segments-types (or segment-type vectors) is a single value or a vector stored in T. An example z( ) may be as follows:
T=0
if(AND(if segment$_i$ is After Peak, if segment$_{i-1}$ is After Peak, . . . , if segment$_{i-1}$ is After Peak)=True)
T=1
if(AND(if segment$_i$ is Before Peak, if segment$_{i-1}$ is Before Peak, . . . , if segment$_{i-1}$ is Before Peak)=False)
where i is the index of the current segment. Each of the operands in the AND( ) operation can be computed by any of Tests A, B.1, B.2 and C. In a variation of Test C, the output of z( ) can be a continuous value between 0 to 1.

Each of Tests A, B.1, B.2 and C are useful in determining where, in a sequence of incoming data values, an event such as a wetness event occurs. The tests are intended to be robust to signal artefact and to produce more reliable results than event detection methods which employ mere threshold detection. The approach adopted in the present invention employs algorithms that have regard to windows of data rather than single points, and which windows are evaluated according to a plurality of data properties which may be either intrinsic to that window, or extrinsic to the window, or both. This approach gives greater substance to the analysis output.

Optimizing Thresholds for after Peak and Before Peak Tests

In an embodiment, it is possible to optimize values for one or more variables employed in the "After Peak" and "Before Peak" tests. These variables include e.g. thresholds: l, $\alpha$, $\beta$, A and B. Values for these variables may be optimised during an assessment or live analysis of incoming sensor data (live-optimization) or in an offline mode (offline optimization). In an offline optimization, the Segment Classifier Function generates the stream of segment types (or segment type vectors) and an optimisation procedure is applied. The optimization procedure determines the value of the variable (or threshold) according to one or more objectives such as (i) correctly identifying the maximum number of the events occurring in the data; (ii) minimising the number of false-positives; (iii) minimizing the number of false-negatives, and (iv) maximising the number of true-negatives. Typically this is an iterative procedure. In a live-optimization procedure the values of the variables are adjusted during the live analysis based on observational feedback data e.g. from a subject who is wearing a sensor pad or an observer who is monitoring the subject e.g. a carer. Thus in the case of wetness sensing for incontinence monitoring and analysis, when an actual voiding event occurs, the wetness event detection system records a time-stamp. The system then applies an optimization procedure to determine the optimized values of control variables or thresholds which give rise to maximising the number of the events being correctly identified, minimising the number of false-positives and false-negatives, and maximising the number of true-negatives.

Figures 7, 8:
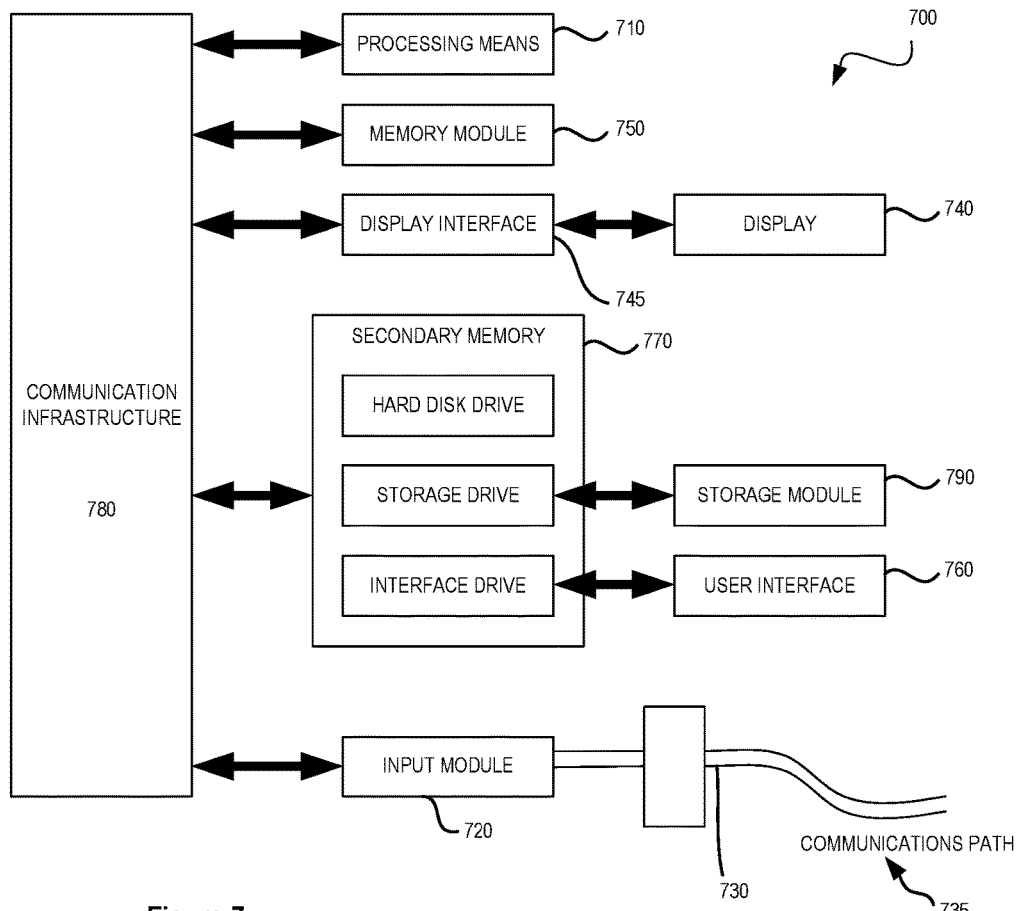
FIG. 7 is a schematic illustration of a wetness event detection system according to an embodiment of the present invention.

Referring now to FIG. 7, there is shown a wetness event detection system 700 for detecting wetness events in sensor data obtained from one or more wetness sensors in a pad worn by a subject. The system 700 includes a communication infrastructure 780 for functional interoperability of the various system components. An input module 720 is configured to receive and optionally pre-process sensor signals from the one or more wetness sensors. Pre-processing may involve e.g. smoothing the data. A storage module 790 stores reference wetness data. The reference wetness data may be pre-processed into a set of Reference Property Vectors, and may be grouped according to e.g. sensor type, patient type (e.g. infant versus adult) or in any other manner considered to improve event analysis.

The system further includes processing means 710 configured to process sensor data obtained from the input module to identify wetness events in the sensor data. The input module may receive the sensor data through any means 730 such as wireless networks, wired networks, USB, flash drive, cloud memory or the like. Sensor data may be provided to the system via communications path 735.

A memory module 750 stores instructions that cause the processing means 710 to perform a method of analysing incoming data as described herein. A user interface 760 is configured to receive inputs from a user or operator. This enables a user or operator to interact with the system e.g. to cause the display means 740 which is communicatively coupled with the processing means via display interface 745 to display wetness event information, or change parameters used in the analysis, append data to reports and the like. It also facilitates input of observational feedback data for use e.g. in life (or offline) optimization of variables/thresholds used in the automated analysis. In an embodiment, the system 700 may also be used to generate Reference Property Vectors as described herein.

Although the present invention has been described and in parts, exemplified in the context of signal analysis for wetness sensor signals and particularly for use in incontinence monitoring, it is to be understood that the analysis and processing methodology described herein has application in a broad range of signal analysis problems where mere threshold detection methods are either unsuitable or inadequate.

Throughout this description and claims, the term "pad" is used. This term is to be interpreted as including diapers, liners, nappies, dressings and other absorbent articles and devices that absorb moisture such as urine, faces, blood, plasma and the like. These may be worn by or applied to adult subjects or babies, children or adolescents. Alternatively/additionally they may be worn by or applied to animal subjects.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components or group thereof.

It is to be understood that various modifications, additions and/or alterations may be made to the parts previously described without departing from the ambit of the present invention as defined in the claims appended hereto.

The invention claimed is:

1. A wetness event detection system for processing sensor signals to detect wetness events in sensor data obtained from one or more wetness sensors in a pad worn by a subject, the system including:
   (a) an input module configured to receive and optionally pre-process sensor signals from the one or more wetness sensors;
   (b) a storage module configured to store reference wetness data;
   (c) processing means configured to process sensor data from the input module to identify wetness events in the sensor data;

(d) a memory module storing instructions that are executable to cause the processor to perform a method of analysing sensor data;
(e) a user interface configured to receive inputs from a user; and
(f) a display means communicatively coupled with the processing means and configured to display wetness event information derived from the processing means,
wherein the processing means processes the sensor data in segments identified using a moving window including one or more boundaries to output a sequence of segment types by extracting one or more properties of an incoming data segment including properties derived from one or more intersections of the incoming data with the one or more boundaries and forming an Unknown Property Vector for each segment of data in the incoming data to identify wetness events in the incoming data,
wherein the sequence of segment types is determined, for each segment, by reference to a set of Reference Property Vectors that are relevant to the Unknown Property Vector.

2. A wetness event detection system according to claim 1, wherein one of the properties represented in an Unknown Property Vector is a sequence identifier representing a sequence number for an event in an event cycle and processing the incoming data in segments includes identifying at least a first subset of Reference Property Vectors that are relevant to the Unknown Property Vector by removing the Reference Property Vectors that have a different event sequence identifier to the event sequence identifier of the Unknown Property Vector.

3. A wetness event detection system according to claim 2, wherein a first k-nearest neighbors of the first subset of Reference Property Vectors is determined by hierarchical elimination based on Euclidean distances calculated for a plurality of selected properties from the segment represented by the Unknown Property Vector and from the corresponding properties of the first subset of Reference Property Vectors.

4. A wetness event detection system according to claim 3, wherein a second k-nearest neighbors of the first subset of Reference Property Vectors is determined by sorting based on the Euclidean distances.

5. A wetness event detection system according to claim 4, wherein a reduced second k-nearest neighbors is determined by:
eliminating a percentage of the furthest Euclidean distances; and/or
eliminating the last rows of a table representing the k-nearest neighbors; and/or
eliminating the neighbors with a Euclidean distance a predetermined percentage greater than a predetermined value.

6. A wetness event detection system according to claim 5, wherein the majority of the segment types in the reduced second k-nearest neighbours is then selected as the appropriate segment type to be ascribed to the Unknown Property Vector.

7. A wetness event detection system according to claim 1, wherein one of the properties represented in an Unknown Property Vector is a sequence identifier representing a sequence number for an event in an event cycle and processing the incoming data in segments includes identifying at least a first subset of Reference Property Vectors that are relevant to the Unknown Property Vector includes allocating a weighting for each of the Reference Property Vectors based on similarity between the sequence identifier of the Reference Property Vector and a sequence identifier of the Unknown Property Vector.

8. A wetness event detection system according to claim 1, wherein processing the incoming data in segments involves applying a logistic regression algorithm to the incoming data, the logistic regression algorithm being derived by i) creating, using a clustering or classification method, one or more candidate vectors representing a reduced set or complete set of Reference Property Vectors, wherein the candidate vectors contain elements representing a degree of belonging to each of a plurality of different segment types; and ii) using the one or more candidate vectors generate the logistic regression algorithm.

9. A wetness event detection system according to claim 1, wherein the Reference Property Vectors are obtained from segmented reference data, and wherein each segment in the reference data has a pre-determined segment type.

10. A wetness event detection system according to claim 1, wherein the moving window has one or more of a width w and a height h; and wherein segments are selected for processing by shifting the moving window by an offset of X seconds.

11. A wetness event detection system according to claim 10, wherein one or more of: the offset X, width w and height h is determined dynamically by one or more of:
applying a function on a plurality of earlier segment types; and
applying a function which is determined by trial and error.

12. A wetness event detection system according to claim 1 wherein a segment type determined for data corresponding to the Unknown Property Vector is a vector having vector elements, wherein each vector element value represents a probability that the Unknown Property Vector belongs to one of a plurality of different segment types.

13. A wetness event detection system according to claim 1, wherein processing the incoming data in segments includes:
a. calculating a Euclidean distance between the sequence identifier in the Unknown Property Vector and the sequence identifier in each of a plurality of Reference Property Vectors; and
b. identifying Reference Property Vectors as being in the first subset where the Euclidean distance calculated is within a limit which is user defined or dynamically determined.

14. A wetness event detection system according to claim 1, including correcting for an imbalance in the number of occurrences of each segment type in the set of Reference Property Vectors relative to the number of vectors in the set of Reference Property Vectors representing the reference data.

15. A wetness event detection system according to claim 1 including processing the sequence of segment types to identify in the sequence, a sub-sequence of segment types represented by a vector having vector elements which each represent a probability that the sub-sequence belongs to one of a plurality of different subs-sequence types.

16. A wetness event detection system according to claim 15, wherein the sub-sequence of segment types correspond to one or more of the following:
i. Flat stage;
ii. Before Peak stage;
iii. event Peak stage; and
iv. After Peak stage.

17. A wetness event detection system according to claim 16, wherein the allocated segment types in the Unknown Property Vectors are segment-type vectors, and processing the sequence of segment-type vectors includes:
  (a) for each segment-type vector in the sequence, determining P by applying a second test function on a subset of segment-type vectors in the sequence;
  (b) if the segment type identified in (a) is Before Peak, comparing P to a first threshold, A, to identify that the sub-sequence of segment types corresponds to the Before Peak stage; and
  (c) if the segment type identified in (a) is After Peak, comparing P to a second threshold, B, to identify that the sub-sequence of segment types corresponds to the After Peak stage.

18. A wetness event detection system according to claim 17 wherein the second test function is applied to one or both of the current segment-type vector and the previous l segment-type vectors in the sequence, and determines which of the segment types referred to in the segment-type vectors has the highest likelihood of occurrence, and from which a vector or value for P is obtained.

19. A wetness event detection system according to claim 17, including one or both of the following features:
  step (b) includes, if the segment type identified in (a) is Before Peak and P is greater than A, satisfying a Before Peak Test for the segment; and
  step (c) includes, if the segment type identified in (a) is After Peak and P is greater than B, satisfying an After Peak Test for the segment.

20. A wetness event detection system according to claim 17, wherein vector elements in a segment-type vector each represent a likelihood of an Unknown Property Vector belonging to each of a plurality of different segment types.

21. A wetness event detection system according to claim 15, wherein processing the sequence of segment types includes:
  (a) for each segment in the sequence, determining T by applying a first test function on a subset of segment type identifiers in the sequence; and
  (b) comparing T to a first threshold, $\alpha$, to identify that the subsequence of segment types corresponds to the Before Peak stage; and/or
  (c) comparing T to a second threshold, $\beta$, to identify that the subsequence of segment types corresponds to the After Peak stage.

22. A wetness event detection system according to claim 21, wherein T is determined by applying the first test function on one or both of the current segment type identifier and the previous l segment type identifiers.

23. A wetness event detection system according to claim 22, wherein the first test function computes the sum, average, maximum, dominant or majority of one or both of the current segment type identifier and the previous l segment types.

24. A wetness event detection system according to claim 22, wherein a variable selected from a group including l, $\alpha$, $\beta$, A and B is determined using one or more of:
  (i) dynamic determination using a function applied over a plurality of earlier segments;
  (ii) an optimization procedure performed during real time analysis;
  (iii) an optimization procedure performed on collected data; and
  (iv) user-definable values.

25. A method according to claim 24, wherein the optimization procedure includes receiving observational data from actual events wherein the value of the variable is determined using an optimization algorithm employing the observational data and one or more objectives selected from the group including:
  (a) correctly identifying the maximum number of the events (true-positives) occurring in the data;
  (b) minimising the number of false-positives;
  (c) minimising the number of false-negatives; and
  (d) maximising the number of true-negatives.

26. A wetness event detection system according to claim 21, including one or both of the following features:
  step (b) includes, if T is greater than or equal to $\alpha$, satisfying a Before Peak Test for the segment; and
  step (c) includes, if T is less than or equal to $\beta$, satisfying an After Peak Test for the segment.

27. A wetness event detection system according to claim 15, wherein an event is detected when the Before Peak Test is satisfied.

28. A wetness event detection system according to claim 1, wherein the properties represented by the property vectors include one or more of: intrinsic properties; extrinsic properties; and demographic information.

29. A wetness event detection system according to claim 1, including the step of smoothing one or both of the incoming data and reference data before extracting one or more properties from the data.

30. A wetness event detection system according to claim 1, wherein the processing means processes the incoming data in segments by applying a function on the Unknown Property Vector and the set of Reference Property Vectors that are relevant to the Unknown Property Vector, wherein the function is selected from a group of methods and algorithms which compute similarity between two or more values or vectors, the group including but not limited to:
  K-nearest neighbours (K-NN);
  Decision trees;
  Support vector machine (SVM);
  Neural network algorithms;
  Distance based methods;
  Euclidean distance-based methods;
  Logistic regression;
  Clustering methods; and
  Classification methods.

* * * * *